United States Patent
Naumann et al.

Patent Number: 5,741,931
Date of Patent: Apr. 21, 1998

[54] PHOSPHEPINIUM SALTS

[75] Inventors: Christoph Naumann; Dieter Regnat, both of Frankfurt am Main, Germany

[73] Assignee: Hoechst AG, Frankfurt, Germany

[21] Appl. No.: 482,825

[22] Filed: Jun. 7, 1995

[30] Foreign Application Priority Data

Jun. 8, 1994 [DE] Germany .................. 44 19 990.2

[51] Int. Cl.$^6$ .................................................. C07F 9/02
[52] U.S. Cl. ......................................... 568/9; 368/12
[58] Field of Search .................................. 568/9, 12

[56] References Cited

U.S. PATENT DOCUMENTS

| | | |
|---|---|---|
| 2,905,717 | 9/1959 | Sarnecki et al. ............... 568/9 |
| 4,943,380 | 7/1990 | Sugiura et al. |

FOREIGN PATENT DOCUMENTS 1235913  3/1967  Germany .

OTHER PUBLICATIONS

S. Gladiali et al., "Tetrahedron: Asymmetry", vol. 5 (4), 511–514 (1994).
K. Yamamoto et al., Japanese Patent 9067 (1955), Chem. Abstracts, 51:17992f (1957).

Primary Examiner—Donald R. Wilson
Attorney, Agent, or Firm—Connolly & Hutz

[57] ABSTRACT

Phosphepinium Salts Thereof

The present invention relates to phosphonium salts of the formula (I)

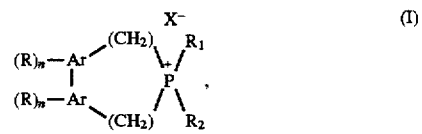

in which Ar—Ar is a biphenyl radical, a 1-phenylnaphthyl radical or a 1,1'-binaphthyl radical, each $CH_2$ group is arranged in the ortho position to the Ar—Ar bond, R is F, an alkyl radical or an alkoxy radical respectively having 1 to 8 carbon atoms, n is an integer from 0 to 4, $R^1$ and $R^2$ are identical or different and, independently of each other, are an alkyl radical having 1 to 10 carbon atoms, a cycloaliphatic radical having 5 to 10 carbon atoms, or are a radical $Ar^1$—$(R^3)_m$, where $Ar^1$ is a phenyl or naphthyl radical, $R^3$ is F, Cl, $CF_3$, $SO_3H$, $SO_3Me$ (Me=Li, Na or K), a dialkylamino radical having 2 to 8 carbon atoms, an alkyl radical or an alkoxy radical respectively having 1 to 8 carbon atoms and m is an integer from 0 to 5, or $R^1$ and $R^2$ together with the P atom form a ring having 4 to 8 members to which may be fused one or two aromatic rings or ring systems including 6 to 10 carbon atoms and $X^-$ is a monovalent anion or the equivalent of a polyvalent anion of a mineral acid, carboxylic acid, sulfonic acid or an alcohol. The invention further relates to a process for the preparation of the phosphonium salts and use thereof.

8 Claims, No Drawings

PHOSPHEPINIUM SALTS

The present invention relates to compounds from the group consisting of phosphonium salts, a process for the preparation thereof and use thereof.

Phosphonium salts have found varied industrial employment. They are suitable, for example, as antistatic compounds (JP 03 81 362; JP 03 74 395; and U.S. Pat. No. 4 943 380), anticorrosion compounds and fire retardants and owing to their variety of forms represent interesting and important building blocks for the preparation of other organic compounds which may contain phosphorus.

In view of the general importance attached to compounds from the group consisting of the phosphonium salts, it is a worthwhile objective to provide novel compounds from this group of substances not only to supplement the spectrum of their applications but also to enrich and enlarge it by adding fine nuances to their physico-chemical properties and variation of structural features.

This object is achieved by phosphonium salts of the formula (I)

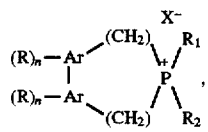

in which Ar—Ar is a biphenyl radical, a 1-phenylnaphthyl radical or a 1,1'-binaphthyl radical, each $CH_2$ group is arranged in the ortho position to the Ar—Ar bond, R is F, an alkyl radical or an alkoxy radical respectively having 1 to 8 carbon atoms, n is an integer from 0 to 4, $R^1$ and $R^2$ are identical or different and, independently of each other, are an alkyl radical having 1 to 10 carbon atoms, a cycloaliphatic radical having 5 to 10 carbon atoms, or are a radical $Ar^1$—$(R^3)_m$, where $Ar^1$ is a phenyl or naphthyl radical, $R^3$ is F, Cl, $CF_3$, $SO_3H$, $SO_3Me$ (Me=Li, Na or K), a dialkylamino radical having 2 to 8 carbon atoms, an alkyl radical or an alkoxy radical respectively having 1 to 8 carbon atoms and m is an integer from 0 to 5, or $R^1$ and $R^2$ together with the P atom form a ring having 4 to 8 members to which may be fused one or two aromatic rings or ring systems including 6 to 10 carbon atoms and $X^-$ is a monovalent anion or the equivalent of a polyvalent anion of a mineral acid, carboxylic acid, sulfonic acid or an alcohol.

The phosphonium salts of the formula (I) are interesting compounds because of their reactivity which may be due to incorporating a $P^+$ ion into a ring system or due to the linking of two ring systems by a $P^+$ ion as a shared member and because of their special structure. The special structure of these compounds shows itself in the fact that very many of these phosphonium salts have one or more centers of asymmetry. In a number of cases, the $P^+$ ion can function as a center of asymmetry. However, in a multiplicity of compounds, centers of asymmetry are also present which result from the $CH_2$—$Ar(R)_n$—$Ar(R)_n$—$CH_2$ group.

The novel phosphonium salts thus also open up access to the corresponding optically active isomers, for example to diastereomeric phosphonium salts or to enantiomeric phosphonium salts which themselves, inter alia, can be used as auxiliaries when asymmetric syntheses are carried out.

Furthermore, the novel phosphonium salts, because of their reactivity and their special structure, are available as building blocks for the preparation of other compounds which may contain phosphorus.

Phosphonium salts of the formula (I) in which Ar—Ar is a biphenyl radical, a 1-phenylnaphthyl radical or a 1,1'-binaphthyl radical and R is an alkyl radical or alkoxy radical respectively having 1 to 4 carbon atoms play a special role since they are comparatively easily synthesized.

This also applies to phosphonium salts of the formula (I) in which n is 0 or 1, in particular n is 0.

Phosphonium salts of the formula (I) are also of interest in which $R^1$ and $R^2$ are identical or different and, independently of each other, are an alkyl radical having 1 to 6 carbon atoms, a cycloaliphatic radical having 5 to 6 carbon atoms or a radical $Ar^1$—$(R^3)_m$, where $Ar^1$ is a phenyl radical, $R^3$ is F, $CF_3$ or an alkyl radical having 1 to 4 carbon atoms and m is 0 or 1, or $R^1$ and $R^2$ together with the P atom form a ring and are $CH_2$—$Ar(R)_n$—$Ar(R)_n$—$CH_2$.

As already mentioned above, $X^-$ is a monovalent anion or the equivalent of a polyvalent anion of a mineral acid, carboxylic acid, sulfonic acid or of an alcohol.

Without making a claim to completeness, $F^-$, $Cl^-$, $Br^-$, $I^-$, $NO_3^-$, $HSO_4^-$, $HCO_3^-$, $BF_4^-$, $PF_6^-$, $H_2PO_4^-$, $ClO_4^-$, $R^4COO^-$, in which $R^4$ is H, an alkyl radical having 1 to 7 carbon atoms or an aryl radical having 6 to 10 carbon atoms, $R^5SO_3^-$, in which $R^5$ is an F, $CF_3$, $CH_3$, phenyl or tolyl radical, or $R^6O^-$, in which $R^6$ is a radical having 1 to 10 carbon atoms may be mentioned as a monovalent anion, or ½ $SO_4^{2-}$, ½ $HPO_4^{2-}$, ½ $CO_3^{2-}$ or ½ of an anion of a dicarboxylic acid having 2 to 6 carbon atoms may be mentioned as an equivalent of a polyvalent anion.

If the phosphonium salts of the formula (I) possess a center of asymmetry and thus fulfil the conditions for the presence of optical isomers, they occur in the (R, S) form, in the (R) form or in the (S) form. Phosphonium salts in the (R) form and the (S) form are of interest in connection with carrying out asymmetric syntheses.

They may be used as optically active building blocks with good prospect of success both in the (R) form or (S) form in order to synthesize in the (R) form or (S) form other compounds which may be optically active and may contain phosphorus.

Phosphonium salts of the formula (I) are of particular interest in which Ar—Ar is 1,1'-binaphthyl and n is 0 or 1, in particular 0. These compounds are not only readily accessible in the (R, S) form but may also be prepared with reasonable expenditure in the (R) form just as in the (S) form.

Without making a claim to completeness, the following compounds may be mentioned as typical representatives of phosphonium salts of the formula (I):

(R,S)-4,4-diphenyl-4,5-dihydro-3H-dinaphtho[2,1-c:1',2'-e]phosphepinium bromide (R)-4,4-diphenyl-4,5-dihydro-3H-dinaphtho[2,1-c:1',2'-e]phosphepinium bromide (S)-4,4-diphenyl-4,5-dihydro-3H-dinaphtho[2,1-c:1',2'-e]phosphepinium bromide (R,S)-4,4-dicyclohexyl-4,5-dihydro-3H-dinaphtho[2,1-c:1',2'-e]phosphepinium bromide (R)-4,4-dicyclohexyl-4,5-dihydro-3H-dinaphtho[2,1-c:1',2'-e]phosphepinium bromide (S)-4,4-dicyclohexyl-4,5-dihydro-3H-dinaphtho[2,1-c:1',2'-e]phosphepinium bromide (R,S)-4,4-diisopropyl-4,5-dihydro-3H-dinaphtho[2,1-c:1',2'-e]phosphepinium bromide (R)-4,4-diisopropyl-4,5-dihydro-3H-dinaphtho[2,1-c:1',2'-e]phosphepinium bromide (S)-4,4-diisopropyl-4,5-dihydro-3H-dinaphtho[2,1-c:1',2'-e]phosphepinium bromide (R,S)-4,4-di-sec-butyl-4,5-dihydro-3H-dinaphtho[2,1-c:1',2'-e]phosphepinium bromide (R,S)-4,4-di-n-butyl-4,5-dihydro-3H-dinaphtho[2,1-c:1',2'-e]phosphepinium bromide 6,6-diphenyl-6,7-dihydro-5H-dibenzo[c,e]phosphepinium bromide bis-[(R,S)-4,5-dihydro-3H-dinaphtho[2,1-c:1',2'-e]phosphepinium bromide 4-methyl-4-phenyl-4,5-dihydro-3H-dinaphtho[2,1-c:1',2'-e]phosphepinium bromide 1,2-bis-{4-phenyl-4,5-dihydro-3H-dinaphtho[2,1-c:1',2'-e]phosphepinium-4-yl}ethane dibromide 6,6-diisopropyl-6,7-dihydro-5H-dibenzo[c,e]phosphepinium bromide 6,6-di-sec-butyl-6,7-dihydro-5H-dibenzo[c,e]phosphepinium bromide 6,6-di-n-butyl-6,7-dihydro-5H-dibenzo[c,e]phosphepinium bromide 6-methyl-6-phenyl-6,7-dihydro-5H-dibenzo[c,e]phosphepinium bromide 6,6-bis(4-sulfophenyl)-6,7-dihydro-5H-dibenzo[c,e]phosphepinium bromide.

The present invention further relates to a process for the preparation of phosphonium salts of the formula (I)

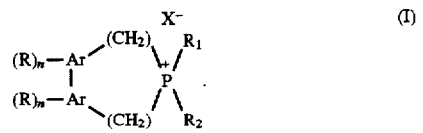

It comprises reacting a compound of the formula (II)

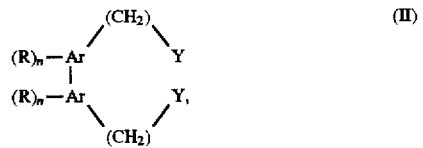

in which Ar—Ar is a biphenyl radical, a 1-phenylnaphthyl radical or a 1,1'-binaphthyl radical, each $CH_2$ group is arranged in the ortho position to the Ar—Ar bond, R is F, an alkyl radical or an alkoxy radical respectively having 1 to 8 carbon atoms, n is an integer from 0 to 4, and Y is Cl, Br, I, or a sulfonate radical $R^5SO_3$, in which $R^5$ is an F, $CF_3$, $CH_3$, phenyl or tolyl radical, with a compound of the formula (III)

in which $R^1$ and $R^2$ are identical or different and, independently of each other, are an alkyl radical having 1 to 10 carbon atoms, a cycloaliphatic radical having 5 to 10 carbon atoms, or are a radical $Ar^1$—$(R^3)_m$, where $Ar^1$ is a phenyl radical or naphthyl radical, $R^3$ is F, Cl, $CF_3$, $SO_3H$, $SO_3Me$ (Me=Li, Na or K), a dialkylamino radical having 2 to 8 carbon atoms, an alkyl radical or an alkoxy radical respectively having 1 to 8 carbon atoms and m is an integer from 0 to 5, or $R^1$ and $R^2$ together with the P atom form a ring having 4 to 8 members to which may be fused one or two aromatic rings or ring systems including 6 to 10 carbon atoms, A is H or $Si(R^7)_3$, where the $R^7$ are identical or different and are each an alkyl radical having 1 to 4 carbon atoms, at 0° to 200° C. in the presence or absence of a solvent and, if appropriate, replacing the anion $Y^-$ for an anion $X^-$, where $X^-$ is a monovalent anion or the equivalent of a polyvalent anion of a mineral acid, carboxylic acid, sulfonic acid or of an alcohol.

The reaction proceeds according to the following equation

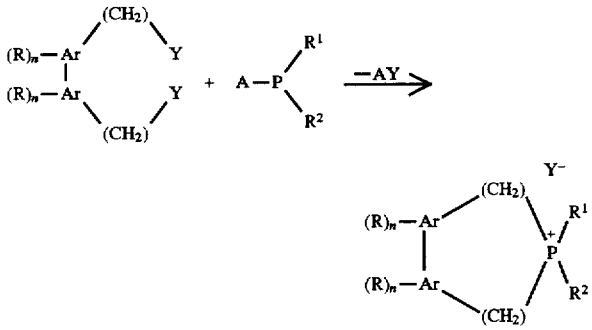

where, if $Y^-$ is not identical to $X^-$, $Y^-$ is then replaced by $X^-$.

An advantage of the process according to the invention is that comparatively readily accessible starting materials can be used. This applies both to the compounds of the formula (II) and to the compounds of the formula (III). A further advantage is that the reaction may be effected without high expenditure in terms of equipment. Furthermore, the reaction proceeds with high selectivity and delivers the desired end products (compounds of the formula (I)) in high yield. The purity of the end products arising in this case is usually so good that a highly pure end product can be obtained by simply crystallizing it out from the reaction mixture directly arising. Additional purification which requires further technical resources and generally causes a reduction in yield can in this case be dispensed with.

Compounds of the formula (II) in which Ar—Ar is a biphenyl radical, a 1-phenylnaphthyl radical or a 1,1'-binaphthyl radical and R is an alkyl radical or alkoxy radical respectively having 1 to 4 carbon atoms play a special role for the process since they are comparatively readily accessible and can be provided in a very large selection.

This also applies to compounds of the formula (II) in which n is 0 or 1, in particular n is 0.

A further advantage of the process according to the invention may be seen in the fact that in a number of cases optically active phosphonium salts of the formula (I) may be prepared both in the (R) form and in the (S) form.

It is generally known that it is very difficult to separate a racemic mixture into enantiomerically pure compounds or even only substantially enantiomerically pure compounds. Such racemate separations are generally connected with a very high expenditure and, furthermore, generally do not lead to success.

By reaction of the compound of the formula (II) in the (R) form or in the (S) form with the compound of the formula (III), the process according to the invention surprisingly opens up a very simple route to the direct preparation of phosphonium salts of the formula (I) in the (R) form and the (S) form. Since the (R) and (S) forms of the phosphonium salts may be synthesized specifically in this manner, a complex racemate separation whose prospects of success are, in addition, highly uncertain, can be dispensed with. The enantiomerically pure or substantially enantiomerically pure phosphonium salts may be produced directly from the reaction mixture by simple crystallization and may be isolated by filtration.

Depending on requirements, a compound of the formula (II) is employed in the (R,S) form, in the (R) form or in the (S) form and the corresponding phosphonium salt is obtained in the (R,S) form, in the (R) form or in the (S) form.

Compounds of the formula (II) in which Ar—Ar is 1,1'-binaphthyl are of particular interest in the (R,S) form, in the (R) form and in the (S) form. In particular, it is of interest to use these compounds in the (R) form or (S) form in order to prepare the corresponding phosphonium salts.

The compound of the formula (II) is reacted with a compound of the formula (III), in particular with a compound of the formula (III) in which $R^1$ and $R^2$ are identical or different and, independently of each other, are an alkyl radical having 1 to 6 carbon atoms, a cycloaliphatic radical having 5 to 6 carbon atoms or a radical $Ar^1$—$(R^3)_m$, where $Ar^1$ is a phenyl radical, $R^3$ is F, $CF_3$ or an alkyl radical having 1 to 4 carbon atoms and m is 0 or 1 or $R^1$ and $R^2$ together with the P atom form a ring and are $CH_2$—$Ar(R)_n$—$Ar(R)_n$—$CH_2$.

The radical A has the importance already mentioned at the outset and is in particular H.

The reaction can be carried out in the presence or absence of a solvent. In a number of cases it has proved to be expedient to carry out the reaction in the presence of a solvent. Usually, the solvent used is a polar aprotic solvent or a nonpolar solvent or a mixture of these solvents.

A polar aprotic solvent which is useful is for example tetrahydrofuran or dioxan and nonpolar solvents which may be used are for example chlorobenzene, dichlorobenzene, toluene, o-xylene, m-xylene, p-xylene, technical-grade mixtures of isomeric xylenes, ethylbenzene or mesitylene or mixtures of these solvents.

Both the compound of the formula (II) and the compound of the formula (III) can be dissolved in the solvent or solvent mixture and then reacted.

The solvent or solvent mixture is conventionally added to the compound of the formula (II) and the compound of the formula (III) is added.

It is generally sufficient to react the compound of the formula (II) and the compound of the formula (III) in a molar ratio of (1 to 2):1, in particular (1 to 1.2):1.

In many cases it has proved to be adequate to carry out the reaction at a temperature of 20 to 160, in particular 50° to 150° C.

The reaction develops particularly simply if the mixture is heated to the boiling point of the particular solvent used and the reaction allowed to proceed at this temperature.

After completion of the reaction, the reaction mixture is cooled, the phosphonium salt generally crystallizing out. The phosphonium salt may then be isolated as a highly pure product by filtration, washing and drying.

If desired, the anion $Y^-$ can be replaced by an anion $X^-$ by carrying out a corresponding double decomposition. This can be achieved, for example, by addition of a salt solution containing the anion $X^-$ to a solution of the phosphonium salt which contains the anion $Y^-$.

The process according to the invention may be carried out both discontinuously and continuously. It can be performed under reduced pressure, at atmospheric pressure or at elevated pressure.

The phosphonium salts of the formula (I) are suitable for use as antistatic compound.

The following examples document the invention without restricting it.

Experimental section

EXAMPLE 1
(R,S)-4,4-diphenyl-4,5-dihydro-3H-dinaphtho[2,1-c:1',2'-e]phosphepinium bromide [(R,S)-2,2'-bis-(diphenylphosphonium bromide)-1,1'-binaphthyl]

Excluding air and moisture, 51.9 g (118 mmol) of (R,S)-2,2'-bis(bromomethyl)-1,1'-binaphthyl are dissolved in 400 ml of absolute toluene at room temperature. To this solution are added dropwise 22 g (118.2 mmol) of diphenylphosphine and the resulting reaction solution is heated to boiling for 8 hours. After cooling, the colorless less solid precipitated is filtered off and washed twice with 100 ml of toluene and 100 ml of low-boiling petroleum ether respectively. The colorless solid is then dried for 4 hours in high vacuum.

Yield: 56.2 g (87.3%)
m.p.: >300° C.
$^1$H-NMR spectrum
(DMSO-$d_6$) 4.05 (dd, $J_{PH}=^2J_{H,H}$=15.5 Hz, 2H, —$CH_2$—); 4.95 (dd, $J_{PH}$=11.4 Hz, $^2J_{H,H}$=15.5 Hz, 2H, —$CH_2$—); 4.97 (d, $J_{PH}$=15.1 Hz, 1H, —$CH_2$—); 7.07 (mc, 2H, aromatic H); 7.35 (mc, 2H, aromatic H); 7.53 (mc, 4H, aromatic H); 7.69 (mc, 4H, aromatic H) 7.82 (mc, 2H, aromatic H); 7.94 (mc, 4H, aromatic H); 8.05 (mc, 4H, aromatic H) ppm.
$^{13}$C-NMR spectrum
(DMSO-$d_6$) 25.9 (d, J=50.7 Hz, 4C, —$CH_2$—); 118.5 (d, J=76.7 Hz, 2C, $C_q$, phenyl); 125.5 (d, J=9.7 Hz, 2C, $C_q$, naphthyl); 126.2–129.5 (12C, CH, naphthyl); 129.8 (d, J=12.1 Hz, 2C, CH, naphthyl); 131.6 (2C, $C_q$, naphthyl); 132.6 (d, J=9.8 Hz, 2C, CH, phenyl); 133.0 (2C, $C_q$, naphthyl); 134.1 (2C, $C_q$, naphthyl); 134.7 (d, J=2.9 Hz, 2C, CH, phenyl) ppm.
$^{31}$P-NMR spectrum
(DMSO-$d_6$) 42.5 ppm
FAB mass spectrum
$M—Br]^+$=465

EXAMPLE 2
(R,S)-4,4-diisopropyl-4,5-dihydro-3H-dinaphtho[2,1-c:1',2'-e]phosphepinium bromide [(R,S)-2,2'-bis-(diisopropylphosphonium bromide)-1,1'-binaphthyl]

Excluding air and moisture, 18.05 g (41.0 mmol) of (R,S)-2,2'-bis(bromomethyl)-1,1'-binaphthyl are dissolved at room temperature in 80 ml of absolute toluene. To this solution are added dropwise 5 g (42.3 mmol) of diisopropylphosphine and the resulting reaction solution is heated to boiling for 8 hours. After cooling, the colorless solid precipitated out is filtered off and washed twice with 50 ml of toluene and 50 ml of low-boiling petroleum ether respectively. The colorless solid is then dried for 4 hours in high vacuum.

Yield: 14.4 g (73.8% of theory)
m.p.: >300° C.
$^1$H-NMR spectrum
(DMSO-$d_6$) 1.28 (mc, 12H, $CH_3$); 2.58 (mc, 2H, methine H); 3.42 (dd, $J_{PH}=^2J_{H,H}$=15.5 Hz, 2H, —$CH_2$—); 4.15 (dd, $J_{PH}$=9.46 Hz, $^2J_{H,H}$15.5 Hz, 2H, —$CH_2$—); 6.92 (mc, 2H, aromatic H); 7.29 (mc, 2H, aromatic H); 7.53 (mc, 2H, aromatic H); 7.83 (mc, 2H, aromatic H); 8.08 (mc, 2H aromatic H); 8.17 (mc, 2H, aromatic H) ppm.
$^{13}$C-NMR spectrum
(DMSO-$d_6$) 16.12 (mc, $CH_3$); 15.12 (d, J=38.2 Hz, 2C, CH); 21.64 (d, J=44.3 Hz, 2C, —$CH_2$—); 126.14 (mc, 4C, CH, aromatic); 126.71 (mc, 2C, CH, aromatic); 127.06 (mc, 2C, $C_q$, aromatic H); 127.90 (mc, 2C, CH, aromatic); 128.41 (mc, 2C, CH, aromatic); 129.39 (mc, 2C, CH, aromatic); 131.79 (mc, 2C, $C_q$, aromatic); 132.85 (mc, 2C, $C_q$, aromatic); 133.43 (mc, 2C, CH, aromatic) ppm.
$^{31}$P-NMR spectrum
(DMSO-$d_6$) 66.67 ppm
FAB mass spectrum
$[M—Br]^+$=397

EXAMPLE 3
(R,S)-4,4-di-sec-butyl-4,5-dihydro-3H-dinaphtho[2,1-c:1',2'-e]phosphepinium bromide [(R,S)-2,2'-bis-(diisobutylphosphonium bromide)-1,1'-binaphthyl]

Excluding air and moisture, 25.4 g (58 mmol) of (R,S)-2,2'-bis(bromomethyl)-1,1'-binaphthyl are dissolved at room temperature in 80 ml of absolute xylene. To this solution are added dropwise 8.74 g (59.8 mmol) of diisobutylphosphine and the resulting reaction solution is heated to boiling for 8 hours. After cooling, the colorless sediment precipitated out is filtered off and washed twice with 80 ml of xylene and then 80 ml of low-boiling petroleum ether respectively. The colorless solid is then dried for 4 hours in high vacuum.

Yield: 22.2 g (75.8% of theory)
m.p.: >300° C.
$^1$H-NMR spectrum
(DMSO-$d_6$) 0.95 (mc, 6H, $CH_3$); 1.23 (mc, 3H, $CH_3$); 1.33 (mc, 3H, $CH_3$); 1.42 (mc, 2H, —$CH_2$—); 1.76 (mc, 1H, CH); 2.05 (mc, 1H, CH); 2.3 (mc, 2H, —$CH_2$—); 3.42 (mc, 2H, —$CH_2$—); 4.18 (mc, 2H, —$CH_2$—); 6.93 (mc, 2H, aromatic); 7.30 (mc, 2H, aromatic); 7.53 (mc, 2H, aromatic); 7.79 (mc, 2H, aromatic); 8.07 (mc, 2H, aromatic); 8.15 (mc, 2H, aromatic) ppm.
$^{31}$P-NMR spectrum
(DMSO-$d_6$) 65.92 ppm
FAB mass spectrum
[M—Br]$^+$=425

EXAMPLE 4

6,6-Diphenyl -6,7-dihydro-5H-dibenzo [c,e]phosphepinium bromide[(R,S)-2,2'-bis(diphenylphosphonium bromide) biphenyl]

Excluding air and moisture, 8.16 g (24 mmol) of (R,S)-2,2'-bis(bromomethyl)biphenyl are dissolved at room temperature in 80 ml of absolute toluene. To this solution are added dropwise 4.47 g (24.0 mmol) of diphenylphosphine and the resulting reaction solution is heated to boiling for 8 hours. After cooling, the colorless less solid precipitated out is filtered off and washed twice with 50 ml of toluene and 50 ml of low-boiling petroleum ether respectively. The colorless solid is then dried for 4 hours in high vacuum.

Yield: 7.7 g (72.1%)
m.p.: >300° C.
$^{31}$P-NMR spectrum
(DMSO-$d_6$) 41.26 ppm
FAB mass spectrum
[M—Br]$^+$=365

EXAMPLE 5

(R,S)-4,4-diphenyl -4,5-dihydro-3H-dinaphtho[2,1-c:1',2'-e]phosphepinium bromide [(R,S)-2,2'-bis-(diphenylphosphonium bromide)-1,1'-binaphthyl]

Excluding air and moisture, 24.8 g (56.7 mmol) of (R,S)-2,2'-bis(bromomethyl)-1,1'-binaphthyl are dissolved at room temperature in 300 ml of absolute toluene. To this solution are added dropwise 15.4 g (59.6 mmol) of trimethylsilyldiphenylphosphine and the resulting reaction solution is heated to boiling for 8 hours. After cooling, the colorless solid precipitated out is filtered off and washed twice with 50 ml of toluene and 50 ml of low-boiling petroleum ether respectively. The colorless solid is then dried for 4 hours in high vacuum.

Yield: 19.5 g (63.1%)
m.p.: >300° C.
$^{31}$P-NMR spectrum
(DMSO-$d_6$) 42.3 ppm

EXAMPLE 6

(R,S)-4,4-dicyclohexyl-4,5-dihydro-3H-dinaphtho[2,1-c:1', 2'-e]phosphepinium bromide [(R,S)-2,2'-bis-(dicyclohexylphosphonium bromide)-1,1'-binaphthyl]

Excluding air and moisture, 11.01 g (25 mmol) of (R,S) -2,2'-bis(bromomethyl)-1,1'-binaphthyl are dissolved in 120 ml of degassed chlorobenzene and the mixture is heated to 100° C. To this solution are added dropwise 7.44 g (37.5 mmol) of dicyclohexylphosphine and the mixture is stirred for a further 5 hours at 100° C. After cooling, the colorless solid is filtered off and washed twice with 50 ml of chlorobenzene and once with 50 ml of low-boiling petroleum ether. The colorless solid is then dried for 4 hours at high vacuum. 10.44 g (75%) of colorless crystals are obtained having a m.p. >300° C.
$^{31}$P-NMR spectrum
(DMSO-$d_6$): δ=59.7 ppm

EXAMPLE 7

(S)-4,4-diphenyl-4,5-dihydro-3H-dinaphtho[2,1-c:1',2'-e] phosphepiniumbromide[(S)-2,2'-bis(diphenylphosphonium bromide)-1,1'-binaphthyl]

Excluding air and moisture, 51.9 g (118 mmol) of (S)-2, 2'-bis(bromomethyl)-1,1'-binaphthyl are dissolved at room temperature in 400 ml of absolute toluene. To this solution are added dropwise 22 g (118.2 mmol) of diphenylphosphine and the resulting reaction solution is heated to boiling for 8 hours. After cooling, the colorless solid precipitated out is filtered off and washed twice with 100 ml of toluene and 100 ml of low-boiling petroleum ether respectively. The colorless solid is then dried for 4 hours in high vacuum.

Yield: 56.2 g (87.3%)
m.p.: >300° C.
$[\alpha]_D^{20}$=−192.5° (measured in N,N-dimethylformamide)

EXAMPLE 8

(S)-4,4-diisopropyl-4,5-dihydro-3H-dinaphtho[2,1-c:1',2'-e] phosphepinium bromide [(S)-2,2'-bis (diisopropylphosphonium bromide)-1,1'-binaphthyl]

Excluding air and moisture, 18.05 g (41.0 mmol) of (S)-2,2'-bis(bromomethyl)-1,1'-binaphthyl are dissolved at room temperature in 80 ml of absolute toluene. To this solution are added dropwise 5 g (42.3 mmol) of diisopropylphosphine and the resulting reaction solution is heated to boiling for 8 hours. After cooling, the colorless solid precipitated out is filtered off and washed twice with 50 ml of toluene and 50 ml of low-boiling petroleum ether respectively. The colorless solid is then dried for 4 hours in high vacuum.

Yield: 14.4 g (73.8% of theory)
m.p.: >300° C.
$[\alpha]_D^{20}$=+139.2° (measured in N,N-dimethylformamide)

EXAMPLE 9

(S)-4,4-dicyclohexyl-4,5-dihydro-3H-dinaphtho[2,1-c:1',2'-e]phosphepinium bromide [(S)-2,2'-bis (dicyclohexylphosphonium bromide)-1,1'-binaphthyl]

Excluding air and moisture, 11.01 g (25 mmol) of (S)-2, 2'-bis(bromomethyl)-1,1'-binaphthyl are dissolved in 120 ml of degassed chlorobenzene and heated to 100° C. To this solution are added dropwise 7.44 g (37.4 mmol) of dicyclohexylphosphine and the mixture is stirred for a further 5 hours at 100° C. After cooling, the colorless solid is filtered off, washed twice with 50 ml of chlorobenzene and once with 50 ml of low-boiling petroleum ether. The colorless solid is then dried for 4 hours in high vacuum.

10.44 g (75%) of colorless crystals are obtained having a m.p. >300° C.

$[\alpha]_D^{20} = +69.2°$ (measured in N,N-dimethylformamide)

We claim:

1. A phosphonium salt of the formula (I)

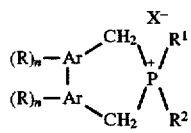

in which

Ar—Ar is a biphenyl radical, a 1-phenyl-naphthyl radical or a 1,1'-binaphthyl radical, each $CH_2$ group is arranged in the ortho position to the Ar—Ar bond, R is F, an alkyl radical having 1 to 8 carbon atoms or an alkoxy radical having 1 to 8 carbon atoms, n is an integer from 0 to 4, $R^1$ and $R^2$ are identical or different and, independently of each other, are an alkyl radical having 1 to 10 carbon atoms, a cycloaliphatic radical having 5 to 10 carbon atoms, or are a radical $Ar^1$—$(R^3)_m$, where $Ar^1$ is a phenyl or naphthyl radical, $R^3$ is F, Cl, $CF_3$, $SO_3H$, a dialkylamino radical having 2 to 8 carbon atoms, an alkyl radical having 1 to 8 carbon atoms, an alkoxy radical having 1 to 8 carbon atoms or $SO_3Me$ wherein Me is Li, Na or K, and m is an integer from 0 to 5, or $R^1$ and $R^2$ together with the P atom form a ring having 4 to 8 members to which may be fused one or two aromatic rings or ring systems including 6 to 10 carbon atoms and $X^-$ is a monovalent anion or the equivalent of a polyvalent anion of a mineral acid, carboxylic acid, sulfonic acid or an alcohol.

2. A phosphonium salt as claimed in claim 1, wherein Ar—Ar is a biphenyl radical, a 1-phenylnaphthyl radical or a 1,1'-binaphthyl radical and R is an alkyl radical or alkoxy radical respectively having 1 to 4 carbon atoms.

3. A phosphonium salt as claimed in claim 1, wherein n is 0 or 1.

4. A phosphonium salt as claimed in claim 1, wherein n is 0.

5. A phosphonium salt as claimed in claim 1, wherein $R^1$ and $R^2$ are identical or different and, independently of each other, are an alkyl radical having 1 to 6 carbon atoms, a cycloaliphatic radical having 5 to 6 carbon atoms or a radical $Ar^1$—$(R^3)_m$, where $Ar^1$ is a phenyl radical, $R^3$ is F, $CF_3$ or an alkyl radical having 1 to 4 carbon atoms and m is 0 or 1, or $R^1$ and $R^2$ together with the P atom form a ring and are $CH_2$—$Ar(R)_n$—$Ar(R)_n$—$CH_2$.

6. A phosphonium salt as claimed in claim 1, wherein $X^-$ as a monovalent anion is $F^-$, $Cl^-$, $Br^-$, $I^-$, $NO_3^-$, $HSO_4^-$, $HCO_3^-$, $BF_4^-$, $PF_6^-$, $H_2PO_4^-$, $ClO_4^-$, $R^4COO^-$, in which $R^4$ is H, an alkyl radical having 1 to 7 carbon atoms or an aryl radical having 6 to 10 carbon atoms $R^5SO_3^-$, in which $R^5$ is an F, $CF_3$, $CH_3$, phenyl or tolyl radical, or $R^6O^-$, in which $R^6$ is a radical having 1 to 10 carbon atoms, or as an equivalent of a polyvalent anion is ½ $SO_4^{2-}$, ½ $HPO_4^{2-}$, ½ $CO_3^{2-}$ or ½ of an anion of a dicarboxylic acid having 2 to 6 carbon atoms.

7. A phosphonium salt as claimed in claim 1, wherein the phosphonium salt is present in the (R,S) form, in the (R) form or in the (S) form.

8. A phosphonium salt as claimed in claim 1, wherein Ar—Ar is 1,1'-binaphthyl and the phosphonium salt is present in the (R,S) form, in the (R) form or in the (S) form.

* * * * *